United States Patent [19]

Bauman et al.

[11] Patent Number: 5,060,678
[45] Date of Patent: Oct. 29, 1991

[54] ARTIFICIAL NAIL AND IMPLANTATION TECHNIQUES

[76] Inventors: Mark L. Bauman, 1524 S. Bowling Green Dr.; Michael M. Goldberg, 1525 Dogwood Dr., both of Cherry Hill, N.J. 08003

[21] Appl. No.: 521,450

[22] Filed: May 10, 1990

[51] Int. Cl.$^5$ .......................................... A45D 29/00
[52] U.S. Cl. .................................... 132/73; 132/200; 623/11; 623/57
[58] Field of Search ................ 132/73, 73.5, 200, 285; 128/81 R, 81 A, 87 A; 606/186, 185, 167; 623/11, 57

[56] References Cited

U.S. PATENT DOCUMENTS

| | | | |
|---|---|---|---|
| 4,180,058 | 12/1979 | Brem | 128/81 A |
| 4,294,241 | 10/1981 | Miyata | 128/156 |
| 4,361,160 | 11/1982 | Bryce | 132/73 |
| 4,445,234 | 5/1984 | Ogunro | 128/81 A |
| 4,453,926 | 6/1984 | Galy | 606/167 |
| 4,559,055 | 12/1985 | Ogunro | 623/11 |
| 4,587,983 | 5/1986 | Wissman et al. | 132/73 |
| 4,751,935 | 6/1988 | Mast et al. | 132/73 |
| 4,759,354 | 7/1988 | Quarfoot | 128/156 |
| 4,819,623 | 4/1989 | Ogunro | 623/11 |
| 4,841,962 | 6/1989 | Berg et al. | 128/DIG. 8 |

FOREIGN PATENT DOCUMENTS 3106522 12/1982 Fed. Rep. of Germany ........ 132/73

OTHER PUBLICATIONS

Article from "Journal of the American Podiatry Association", Stanford Rosen, D.P.M.; *Prosthetic Nail Plate*, Jul. 1970, pp. 283-284.

"Journal of Biomedical Materials Research", Christian Grosse-Siestrup and Klaus Affeld, *Design Criteria for Percultaneous Devices*, 1984, pp. 357-382.

"Annals of Plastic Surgery", Peter J. van Mullem, *Porous Acrylic Cement : Evaulation of a Novel Implant Material*, pp. 576-582.

Scanning Microscopy, vol. 2, No. 2, 1988, Charles J. Doillon *Fibroblast and Epiderman Cell-Type I Collagen Interactions.*

"Journal of Biomechanical Engineering", Charles J. Doillon, Relationship Between Mechanical Properties and Collagen *"Structure of Closed and Open Wounds"*, vol. 110, Nov. 1988.

"Calcified Tissue International" (1988), 42:321-325 *Reconstituted Bovine Skin Collage Enhances Healing of Bond Wounds in the Rat Calvaria.*

"Collagen Rel. Res." vol. 1/1988, pp. 83-100; *The Influence of Healing on the Wound Healing Response to Collagen Implants in vivo.*

"JBCR", vol. 9, No. 4, Steven T. Boyce, Ph.D., et al. *Reduced Wound Contraction After Grafting of Full--Thickness Burns with a Collagen Coverage with Biobrane.*

"World Journal of Surgery", 8, 970-974, 1984, *The Use of PMMA Beads in Recurrent High Anal Fistula: A Preliminary Report.*

"Scanning Electron Microscopy/1985/II", pp. 897-903, *Collagen Deposition During Wound Repair.*

"Proc. Natl. Acad. Sci, U.S.A.", vol. 86, pp. 933-937; Feb. 1989, *Synthesis and characterization of a model extracellular matrix that induces partial regeneration of adult mammalian skin.*

"Journal of the American Academy of Dermatology", vol. 12, No. 2, Part 2, Feb., 1985, Lyle S. Leipziger, B. S. *Dermal wound repair: Role of collagen matrix implants and synthetic polymer dressings.*

(List continued on next page.)

Primary Examiner—John J. Wilson
Assistant Examiner—Frank A. LaViola
Attorney, Agent, or Firm—Connoly & Hutz

[57] ABSTRACT

An artificial nail includes an acrylic top layer mounted on a collagen support layer in the form of a mesh. The proximal end of the nail includes a plurality of anchor points, preferably three semi-circular anchor points. The proper size nail is selected by use of sizers. The toe or finger is prepared for implantation of the artificial nail by a puncturing tool which has a pattern of tines on its flat base.

16 Claims, 1 Drawing Sheet

OTHER PUBLICATIONS

J. Biomed. Mater. Res.: Applied Biomaterials, vol. 22, No. A2, 191–206 (1988) *Wound healing using a collagen matrix: Effect of DC electrical stimulation.*

Biomaterials, 1986, vol. 7 Jul., pp. 277–282, *Comparative biotolerance of polyacrylamide-agarosde gel, silicone rubber and microporous PTFE as soft tissue implants* David E. Taylor.

J. Oral Maxillofax Surg. 46:971–978, 1988, C. N. Bertolami, D.D.S. *Healing of Cutaneous and Mucosal Wounds Grafted Wth Collagen-Glycosaminoglycan/-Silastic Bilayer Membranes: a Preliminary Report.*

Otolaryngologic Clinics of North America—vol. 17, No. 2, May 1984, Milos Chvapil, M.D.; Ph.D., *SDcar Formation: Physiology and Pathological States.*

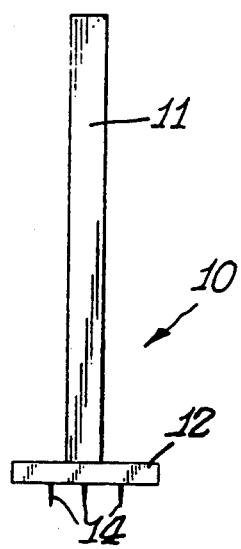
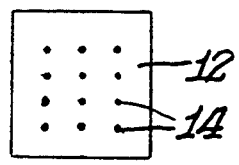
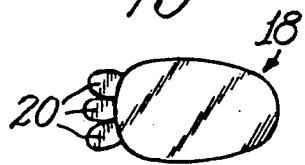
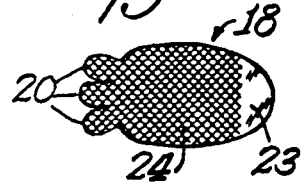
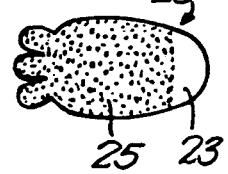
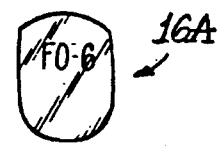
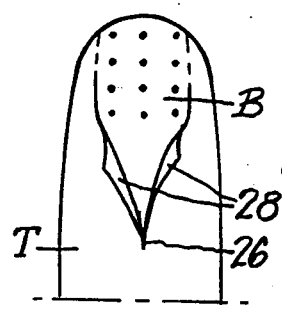
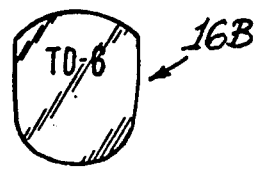
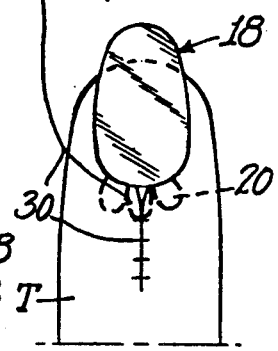
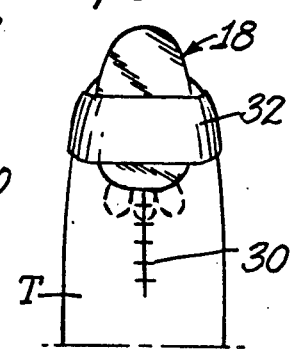

ARTIFICIAL NAIL AND IMPLANTATION TECHNIQUES

BACKGROUND OF INVENTION

Total nail excisions with matricectomies have been done for many years by various disciplines in the medical sciences. Most common conditions that warrant such a procedure have classically been deformity due to onychomycoses and severe onychodystrophies, all conditions representing chronic reoccurrence. The techniques in performing the radical excision of nails has been varied between surgical excision of the matrix and excision of the nail plate to chemosurgical destruction, and most recently, fulgeration by laser of the matrix cells. All surgical procedures have generally accomplished their aims, that is to destroy the nail so there is no regrowth. Unfortunately, this has left the patient with a dilemma: the eradication of the condition (whatever it may have been) at the expense of cosmetic consideration, as well as some degree of discomfort, though not "pain" per se.

Since our society holds beauty and physical perfection in such high regard, the lack of a nail on either a foot or hand can represent a significant detriment to one's perception of physical well being. The method to date in dealing with this problem for those so concerned has been to minimize the untoward cosmetic effect by coating the cornifed nail bed with nail polish or, in the case of feet, foregoing the use of various shoewear which calls attention to the appearance of the toes. Specifically with the feet an additional problem is identified relative to cosmetic needs. Dress shoewear for females is generally designed to enhance and to accentuate the female physique; shoewear plays a very important role in one's overall appearance. Many styles of shoes strive to appeal to that which is aesthetic over that which is functional. Since female feet are thus more exposed than corresponding male feet in terms of shoewear, this problem can be identified more acutely with the female population.

Attempts have been made to provide an artificial nail for cosmetic purposes. Rosen, in 1970, described the use of a monomer-polymer prosthetic nail plate temporarily attached with gum spirits to the underlying healed nail bed. The nail plate was custom designed on a model which was then used on the actual toe. Many doctors have since recommended the use of commercial artificial finger nails, adapted to toes and attached to the surrounding skin by varying methods of adhesion.

SUMMARY OF INVENTION

An object of this invention is to provide an artificial nail and surgical implantation techniques which meets the needs indicated above.

A further object of this invention is to provide such a nail which may be part of a kit having a plurality of such nails as well as a puncturing tool and sets of sizers.

In accordance with this invention, the artificial nail is made of two layer structures. The top layer is formed from a material such as an acrylic which provides the proper cosmetic appearance. The bottom layer acts as a cohering layer and is preferably made of a material such as collagen which would be compatible with the bed of the finger or toe to which the nail is implanted. The proximal end of the nail includes a plurality of anchor points, such as three semi-circular anchor points which would be implanted under the skin flaps of the nail bed.

The collagen mesh in the preferred practice of this invention extends distally to an area short of the free edge of the acrylic layer. The acrylic layer thins or tapers from the proximal end distally to the anchor points.

In accordance with a preferred practice of this invention, sets of sizers are provided, generally corresponding to the different types of nails that would be replaced so as to determine the proper size, shape and width of the artificial nail. A puncturing tool is also provided which includes a pattern of tines on its flat base to prepare the nail bed for reception and implantation of the artificial nail.

THE DRAWINGS

FIG. 1 is a side elevation view of a puncturing tool used in the practice of this invention;

FIG. 2 is a bottom plan view of the puncturing tool shown in FIG. 1;

FIG. 3 is a top plan view of an artificial nail in accordance with this invention;

FIG. 4 is a side elevation view of the artificial nail shown in FIG. 3;

FIG. 5 is a bottom plan view of the artificial nail shown in FIGS. 3-4;

FIG. 6 is a bottom plan view similar to FIG. 5 of a modified form of an artificial nail;

FIG. 7 is a rear elevation view of an artificial toenail in accordance with this invention;

FIGS. 8 and 8A are top plan views of sizers used in the practice of this invention; and FIGS. 9-11 are top plan views showing steps used for implanting an artificial nail in accordance with this invention.

DETAILED DESCRIPTION

The present invention is directed to the implantation of artificial nails. It is to be understood that the practice of this invention may be accomplished for either toenails or fingernails.

In general, the invention involves selecting the proper nail by means of a sizer. A puncturing tool is then utilized to prepare the nail bed for reception of the nail. After the proper nail has been selected and the nail bed prepared the nail is then implanted in place. The invention may be practiced by utilizing an established technique nail matricectomy which is performed by chosen method on the patient's toe or finger. The patient's toe or finger is allowed to heal as per standard techniques. For example, a minimum of 3-6 months is preferred to ensure within reason a non-occurrence of the natural nail. As is applicable, the replacement nail surgery is performed at this time. A puncturing tool or instrument 10 is utilized which will create small uniform puncture holes in the nail bed and underlying tissue to the skin at the most proximal portion of the nail (approximately 0.5 cm proximal to the level of the former cuticle). This instrument 10 has the gross appearance of a microtome, with handle 11 having a flat base 12 housing three rows of four tines 14 which will penetrate the tissue at a fixed level causing small microbleeding. Handle 11 is about three to four inches long and base 12 is about one inch square. The instrument 10 is autoclavable or may be made disposable to be included with the standard nail replacement kit.

In the kit, along with such an instrument 10, is the actual replacement nail material and assorted sizers. These sizers 16 are preferably packaged as per the type of nail to be replaced (i.e. great toenail replacement kit and lesser toenail replacement kit). The sizers are used as a vehicle for allowing the customizing of the individual nail in question. Once the sizer has been used to determine the exact shape, size and width of the required replacement nail, an appropriate "implant nail" 18 can be selected from its particular packaging. The sizers or templates 16, being made out of an autoclavable plastic are reused as needed; the actual nails 18 since packed sterile, may only be used once. A suitable numbering code is as follows: GT 0 to 6 indicating relative size and shape of the Great Toe nail implant with 0 being the largest and 6 being the smallest; and LT 0 to 6 with LT being "lesser toe" and the same gradation numerically. Alternatively, similar gradations would apply for thumb (T 0-6) and fingers (F 0-6). FIGS. 8 and 8A show such respective sizers 16A and 16B.

The artificial nail implants 18 are preferably made of a standard nail thickness acrylic material with a plurality, preferably three semicircular anchor points or extensions 20 found proximally. The artificial nail 18 is actually constructed as a bilayer of acrylic on the top acting as a cosmetic layer 22 and collagen mesh on the underside as a cohering layer 24. This collagen mesh 24 extends distally to approximately 0.5 cm to the free edge 23 of the nail (and can be made longer, if desired, for toenails and custom shaped and sized fingernails) and proximally to and includes the semicircular anchor points. See FIG. 5. The acrylic upper surface 22 thins proximally to where the anchor points 20 are, so as not to be overly thick for insertion under the skin. The collagen mesh 24 is also embedded into the upper surface of the three anchor points 20. The acrylic surface, as well as the anchor points' surfaces, top and bottom, are industrially pre-roughened in order to allow for better ingrowth of the collagen. The roughening creates a meshwork surface that allows for some porocity and better ingrowth of the collagen meshwork. See FIG. 5. The toenails are very slightly curved in the transverse axis, while the fingernails are slightly curved in the longitudinal axis.

The requirements for the surgery in terms of material and instrumentation to summarize would be as follows: an instrument 10 to make the small performations in the underlying nail bed and soft tissue (dubbed an "onychiotine") which is made and packaged for single use (disposable) or multiple use (autoclavable); sizer kits for both the great toenail and lesser toenails (possibly the great toenail with modification doubling as use of the thumbnail and lesser toenail implants for certain fingers); and finally the implantable nails themselves, being constructed of a sterilely packaged bilayer material 18 consisting of an acrylic upper surface 22 and a collagen meshed undersurface 24.

The following procedure may be used for implanting a nail 18 to a toe. With the patient prepped and draped in the usual sterile manner, after anesthesia has been effected and an Esmarche tourniquet applied to the required toe T, a 1 cm vertical incision 26 is made over the skin at the level proximal to the eponychium (cuticle). The incision is made equidistant from each lateral edge of the nail creating two flaps 28 which are undermined and reflected both medially and laterally. A sizer 16 is introduced to determine both the shape and size of the required nail implant 18 (relative to the surrounding skin; the sizer has no anchor points which would need to be "templated"). With this being accomplished; the appropriate sterile artificial nail 18 is readied for use. An onychiotine or tool 10 is then utilized to create microvascular bleeding to the exposed nail bed B in a patterned fashion. See FIG. 9. The onychiotine 10 is used to approximately 0.25 cm proximal to the free edge of the nail bed and proximally to include the area of soft tissue under the proximal skin flaps 28. If after follow-up there appears to be a lack of cohesion between nail implant (Onychioplant) and nail bed B there may be a need to infuse a small amount of collagen (e.g. Zymagen implant). The proper nail implant 18 is then applied with instrumentation so the anchor points 20 lay under the reflected skin flaps 28 and the free edge of the implant corresponds to an acceptable level relative to the end of the toe. As shown in FIG. 10, the skin flaps 28 are then reapproximated utilizing skin suture 30, preferably 5-0 or 6-0, and a pressure bandage 32 is applied to the nail plate providing a stable environment for the cohesion (not adhesion) of the nail plate to the nail bed. See FIG. 11. The dressing 32 is changed by the surgeon after the third to fifth day, and appropriate dressing changes thereafter. At such time as the nail 18 is stable to the underlying bed, the nail 18 may be polished or minimally modified as needed by grinding. The new nail 18 should be protected for 1-6 months (after initial use follow-up determines appropriate time), preferably with a soft removable cover such as Tubefoam with open hook closures.

As the nail 18 is attached to the nail bed B by cohesion, (i.e. the nail collagen and collagen of the soft tissue meshes and becomes one) the bond is permanent and thus is stronger and more mechanically sound than simple adhesion. The three anchor points 20 on the proximal edge take up most of the mechanical stress which mimics a natural nail. The bonding which occurs under the nail plate is similar to what is found naturally that being the microadhesions which secure the nail plate to the underlying nail bed. Fibroblasts are generated from the created wound made by the Onychiotine and should migrate along the collagen fibers which are adhered to the roughened, mesh-configured surface porous implant. Acrylic is chosen as the base material due to its inherent strength, history of biocompatibility, its ability to withstand erosion and abrasion, and its ability to be colored either industrially (to create the original color) or by items such as nail polish. Collagen is chosen as the cohering material due to its natural ability to act as a wound mesh and network, and since cohesion is created, it would act as a biological "glue". It also could be utilized as a space filler between nail and nail bed in this procedure should the nail not be able to accurately conform to a severely misshapened nail bed; thus to prevent a gapping problem. There may also be a need to pre-test patients prior to the use of the collagen, regardless of the need for the Zymagen infusion, via subcutaneous injection of Zymagen as prescribed by the Collagen Corporation in their literature for Zymagen implant or Keragen implant. Finally, if it is found that not enough cohesion or strength is generated by our model as is described in the proceeding pages, a collagen sponge 25 may be able to be adhered to the nail to provide greater collagen ingrowth as shown in FIG. 6.

The procedure itself has no untoward effects, save the possible sensitivity one may have to the material (but the lack of a nail often creates a greater sensitivity which is quite evident post-operatively with patients who learn to accept it). If the nail 18 would need to be removed, an additional surgical intervention would be required. In the case of injury to the toe where the nail implant was partially destroyed or damaged, a replacement nail could be reapplied in the same fashion as the original implant surgery. The procedure affords the patient cosmetic relief for a perceived unsightly condition and enhances both beauty and self-assuredness and a general feeling of comfort in society. The invention provides a more permanent and acceptable alternative to the current status quo; it also increases by its very design and application, a higher level of acceptance on the part of the general population and affords a cosmetic as well as functional (as relates to sensation) correction of those who desire.

What is claimed is:

1. An artificial nail for a toe or finger comprising a preformed bilayer structure having a distal end and a proximal end, a plurality of anchor extensions at said proximal end for insertion beneath skin flaps at the nail bed of the toe or finger to which the nail is implanted, said bilayer structure including a top cosmetic layer, said bilayer structure including a cohering layer mounted to the underside of said top layer for causing said bilayer structure to cohere to the nail bend, and said anchor extensions extending outwardly from and generally coplanar with said cohering layer for extending directly into a lateral incision made in the nail bed beneath the skin flaps at the nail bed.

2. The nail of claim 1 wherein said cohering layer covers the underside of said top layer from the edge of said proximal end to a location immediately inward of said distal end to leave a free edge of said top layer at said distal end with no cohering layer thereat.

3. The nail of claim 2 wherein each of said anchor extensions is of generally semicircular shape.

4. The nail of claim 3 wherein there are three of said anchor extensions.

5. The nail of claim 4 wherein said cohering layer is made of a collagen material.

6. The nail of claim 5 wherein said cohering layer is of mesh form.

7. The nail of claim 5 wherein said cohering layer is made of a collagen sponge material.

8. The nail of claim 5 wherein said top layer is made of an acrylic material.

9. The nail of claim 8 wherein said top layer is thicker at said distal end than at said proximal end.

10. The nail of claim 9 wherein said top layer tapers in thickness.

11. The nail of claim 1 wherein each of said anchor extensions is of generally semicircular shape.

12. The nail of claim 1 wherein said cohering layer is made of a collagen material.

13. The nail of claim 12 wherein said cohering layer is of mesh form.

14. The nail of claim 1 wherein said top layer is made of an acrylic material.

15. The nail of claim 1 wherein said top layer is thicker at said distal end than at said proximal end.

16. A method of implanting an artificial nail to the nail bed of a toe or finger comprising the steps of making an incision over the skin at the proximal end of the nail bed to create a pair of flaps, placing a sizer selected from a set of sizers on the nail bed to determine the appropriate sizer for that nail bed, selecting an artificial nail corresponding in size and shape and width to the selected sizer, puncturing the nail bed with a puncturing tool, inserting the artificial nail on the punctured nail bed with a plurality of anchor stops at the proximal end of the artificial nail being inserted under the flaps, suturing the flaps closed, and cohering the artificial nail to the nail bed.

* * * * *